US008353223B2

(12) United States Patent
Bunker

(10) Patent No.: US 8,353,223 B2

(45) **Date of Patent: *Jan. 15, 2013**

(54) TRACE PARTICLE COLLECTION SYSTEM

(75) Inventor: Stephen N. Bunker, Wakefield, MA (US)

(73) Assignee: Implant Sciences Corporation, Wilmington, MA (US)

( * ) Notice: Subject to any disclaimer, the term of this patent is extended or adjusted under 35 U.S.C. 154(b) by 1223 days.

This patent is subject to a terminal disclaimer.

(21) Appl. No.: 12/152,441

(22) Filed: May 14, 2008

(65) Prior Publication Data

US 2012/0137792 A1 Jun. 7, 2012

(51) Int. Cl.
*G01N 1/00* (2006.01)

(52) U.S. Cl. ..................................................... 73/864.33

(58) Field of Classification Search ............... 73/863.22, 73/863.23; 239/551

See application file for complete search history.

(56) References Cited

U.S. PATENT DOCUMENTS

| | | | | |
|---|---|---|---|---|
| 4,767,602 | A * | 8/1988 | Johnson | 422/535 |
| 5,931,721 | A * | 8/1999 | Rose et al. | 451/89 |
| 5,931,724 | A | 8/1999 | Perlov et al. | |
| 6,314,601 | B1 * | 11/2001 | McClain et al. | 8/158 |
| 6,321,588 | B1 * | 11/2001 | Bowers et al. | 73/24.01 |
| 6,619,922 | B2 * | 9/2003 | Illingworth et al. | 416/185 |
| 6,828,795 | B2 | 12/2004 | Krasnobaev et al. | |
| 6,861,646 | B2 | 3/2005 | Motchkine et al. | |
| 6,870,155 | B2 | 3/2005 | Krasnobaev et al. | |
| 6,888,128 | B2 | 5/2005 | Krasnobaev et al. | |
| 6,978,657 | B1 * | 12/2005 | Baumann et al. | 73/28.04 |
| 7,098,672 | B2 | 8/2006 | Belyakov et al. | |
| 7,244,288 | B2 | 7/2007 | Belyakov et al. | |
| 8,122,756 | B2 * | 2/2012 | Bunker | 73/12.08 |
| 2003/0155504 | A1 | 8/2003 | Motchkine et al. | |
| 2006/0214580 | A1 | 9/2006 | Bunker et al. | |
| 2007/0158447 | A1 | 7/2007 | Bunker | |
| 2007/0215725 | A1 * | 9/2007 | Bunker et al. | 239/551 |

FOREIGN PATENT DOCUMENTS

| | | | |
|---|---|---|---|
| CA | EP0896213 | A2 * | 2/1999 |
| DE | 101 61 784 | A1 | 6/2003 |
| EP | 0 896 213 | A2 | 2/1999 |
| EP | 0 896 213 | A3 | 2/1999 |
| RU | 2279051 | C2 | 6/2006 |
| RU | 70 369 | U1 | 1/2008 |
| WO | WO 00/16064 | | 3/2000 |

OTHER PUBLICATIONS

Bowers, William, D. "Pulsed Air Sampler", Patent Cooperation Treaty Application No. WO 00/16064 Mar. 23, 2000.*

Liquid Carbon Dioxide Material Safety Data Sheet provided by Air Liquide, p. 1. Aug. 31, 2005.*

* cited by examiner

*Primary Examiner* — Peter Macchiarolo

*Assistant Examiner* — Natalie Huls

(74) *Attorney, Agent, or Firm* — Muirhead and Saturnelli, LLC

(57) ABSTRACT

A trace particle collection system accumulates trace particles of those materials that are adhering to target surfaces. The particles are removed from the surface, transported and collected in a particle collection medium, and then provided to a detection instrument. Trace particles are often bound tenaciously to the target surface, and simple techniques, such as blowing air, will either remove only the largest particles or none at all. The removal of trace particles is described which utilizes an aerosol mixture of frozen carbon dioxide aerosol particles in a gas stream to impact and more efficiently remove the target particles from the surface.

22 Claims, 4 Drawing Sheets

220 217 221 223 215 225 212 211 218 213 222 216 224 219 214 226 200

TRACE PARTICLE COLLECTION SYSTEM

BACKGROUND OF THE INVENTION

1. Field of the Invention

This invention relates to detection of trace chemicals, and more particularly to collection of particles of substances from a surface in order to provide the release, transport, and capture of the particles.

2. Description of Related Art

There exist a wide variety of chemical analysis instruments that are capable of detecting and identifying target particles of trace chemicals ("target chemicals") once the sample of particles is transported to the instrument and subsequently vaporized. Examples include, but are not limited to, ion mobility spectrometers, mass spectrometers, gas chromatographs, surface acoustic wave sensors, cantilever beam sensors, and electron capture detectors. Similarly, there are several ways that may be utilized to transport the target particles to the instrument, some of which are incorporated within the instrument and some which may require an operator to perform the transfer. Examples include, but are not limited to, mechanically transporting a collected sample to the instrument, vacuum collection of vapor or particles, and vortex vacuum sampling.

The target particles begin by being attached to a surface by weak chemical bonds, van der Waals forces, mechanical attachment in a fibrous structure or porosity, adhesive forces, electrostatic attraction, or entrainment in a sticky material, such as grease. For some target chemicals, such as narcotics and explosives, the surface adhesion forces can be relatively strong, making the target particles difficult to remove by simple, low momentum transfer methods, such as blowing a puff of air. Removal of such strongly adhered target particles by blowing air is usually successful only for the largest and heaviest target particles that present the greatest surface area to the blowing air. In general, blowing air does not readily remove target particles of explosives or narcotics from rigid surfaces, only from flexible surfaces, such as cloth, where the fluttering motion of the material and the high porosity provides the means to mechanically dislodge the target particles. Even with cloth, the blowing air stream usually requires a very high velocity flow to have any effect and then only for the largest target particles, so the process is very inefficient.

In some cases, the process of taking a sample begins with an operator or a machine physically wiping an absorbent, often textured substance, such as chemical filter paper, onto the surface to be tested (the "target surface"). Target particles of the chemical of interest may then be transferred and concentrated on, or in, the surface texture of the absorber by the mechanical action of the wiping. This intermediate absorber is then brought to the vicinity of the detection instrument to make a measurement. The wiping method generally works reliably and efficiently but can be costly, because the media usually has to be replaced often, and a trained operator is often required. In addition, operators become tired and fail to wipe in exactly the same way each time.

There are many applications in which it may be desirable to avoid having to manually wipe a surface. These include, for example, sampling without an operator, large area sampling, remote sampling, robotic sampling, surfaces where physical contact is unacceptable, and situations in which the frequent replacement of wiping materials is not acceptable, possibly due to high cost. In these cases a better method of dislodging target particles from the surface than simply blowing air may be desirable.

A non-contact apparatus for cleaning a silicon semiconductor wafer is known. See for example, U.S. Pat. No. 5,931,721 by Rose et al., "Aerosol Surface Processing". Aerosols of liquids or solids are used to abrade contamination particles and films from a silicon wafer surface without damaging the semiconductor devices previously constructed on the wafer. This apparatus is for cleaning a wafer, and no effort is made to capture the resultant particles for chemical analysis. In addition, other cleansing features, such as rinsing the wafer, are required in addition to the aerosol surface processing.

SUMMARY OF THE INVENTION

In accordance with one aspect of the system described herein is an apparatus for dislodging and collecting target particles from a target surface. The apparatus includes a reservoir of pressurized liquid carbon dioxide ("$CO_2$") for an aerosol, at least one pulsed valve, at least one liquid carbon dioxide expansion chamber, at least two nozzles for directing the aerosol mixture at a target surface that are in communication with the source of pressurized liquid carbon dioxide, the at least one pulsed valve, and the at least one expansion chamber, a vacuum providing a suction flow into an orifice that entrains frozen carbon dioxide ("dry ice") particles from the aerosol mixture and target chemical particles dislodged by an impact of the dry ice particles from the aerosol mixture, and a collecting medium for accumulating the particles entrained in the suction flow. The expansion chamber may include a chamber with solid walls immediately downstream of said pulsed valve. The suction flow into an orifice may be surrounded circumferentially by a spinning vortex flow. The collecting medium may include at least one of a filter, chemically coated adsorbing surface, metal mesh, three dimensional woven metal, metal wire, metal foil, metal and electrical insulator laminate, or a resistive coating on a substrate. The collecting medium may be an electrode of an electric field disposed substantially perpendicular to the direction of gas flow through said collecting medium. The collecting medium may be disposed upstream of said orifice. The collecting medium may be disposed within said orifice. The reservoir may be a pressurized tank of liquefied carbon dioxide. When the reservoir is a pressurized tank of liquefied carbon dioxide, solid particles for an aerosol mixture may be formed by the freezing action during the free expansion of said liquefied gas in an expansion chamber in which a first portion of the liquid is vaporized by absorbing energy and a second portion of the liquid is frozen into particles by releasing energy. The aerosol mixture may be delivered in pulses at predetermined time intervals, and the aerosol particles may be delivered in accordance with delivery of the pressurized $CO_2$ gas that accompanies the formation of the dry ice aerosol particles in the expansion chamber.

In accordance with another aspect of the system described herein is a method for dislodging and collecting target particles from a target surface. An aerosol mixture including frozen carbon dioxide aerosol particles dispersed in a pressurized gas is provided. The aerosol mixture is directed at the target surface including the target particles. The aerosol particles impact the target particles causing removal of the target particles from the target surface and causing the target particles to be included in a flow of the pressurized gas with the aerosol particles. Also provided is a suction flow into which the flow of the target particles, the aerosol particles, and the pressurized gas are directed. The particles entrained in the suction flow are collected on a filter substrate. The method may also include delivering the pressurized gas and aerosol mixture in timed pulses, and delivering the aerosol particles in accordance with the timed pulses. The method may also include combining the pressurized gas with the aerosol particles to form the aerosol mixture. The suction flow may be created utilizing a vacuum suction flow into an orifice. The vacuum suction flow into an orifice may be bounded circumferentially by a spinning vortex. The pressurized gas and aerosol mixture may be delivered at a timed pulse between 0.01 seconds and 1 second.

An aerosol generator may be interfaced to other components of a system used in conjunction with a trace chemical detector. The use of an aerosol mixture to remove target particles may be accomplished without the operator or a wipe contacting the target surface.

An embodiment of a particle removal system may include a particle removal component, a particle transport component, and a particle collection component. The particle removal component may include an aerosol generator that is provided with a source of pressurized gas to blow the frozen carbon dioxide aerosol particles towards a target surface that may be contaminated with traces of particles of target chemicals. The source of pressurized gas may be operated pulsed. A typical pulse may be between 0.01 seconds and 1 second. A plurality of at least two nozzles may be provided for guiding the aerosol mixture towards a focal point a short distance beyond the target surface such that this point is the object of the particle transport component of the particle removal system.

The frozen carbon dioxide aerosol particles may be solid but not liquid. The frozen carbon dioxide particles may sublime at ambient temperature. The sublimation of the frozen carbon dioxide aerosol particles ensures that they will disappear from the particle collection component as well as the surrounding environment soon after the pulse.

The aerosol generator may generate the particles for the aerosol by the free expansion of liquefied carbon dioxide into atmospheric pressure, which produces frozen carbon dioxide particles. Said frozen particles may be further entrained and mixed with the simultaneously produced carbon dioxide gas or optionally combined with a second flow from a separate source of pressurized gas used as an accelerant.

The frozen carbon dioxide aerosol particle material may be selected to provide no significant damage to the target surface. Aerosol particles with a high hardness, such as silica or alumina, are abrasive and may damage the target surface as a result of the high velocity impact. Carbon dioxide is an oxide and has no flashpoint, which may be noted as an important characteristic when working with finely divided materials.

The frozen carbon dioxide aerosol mixture may be nontoxic and harmless to humans and animals, as long as the aerosol is not directed into the eyes. The frozen carbon dioxide aerosol mixture may be pulsed to avoid excessive emissions into a confined space, since the carbon dioxide gas residue may displace the oxygen in air.

The frozen carbon dioxide aerosol particles may impact the target particles on the target surface and provide sufficient momentum transfer to dislodge the target particles from the target surface and become entrained in a puff of gas transporting the aerosol particles. The dislodged target particles and aerosol particles may then be collected by the particle transport component. The frozen carbon dioxide aerosol mixture may release target particles by at least one of: physical impact between the aerosol particle and the target particle, sudden sublimation producing a local pulse of gas when the aerosol particle contacts a surface at room temperature, the pulse of pressurized gas accompanying the aerosol mixture, and cooling the target particle such that its adhesion properties are changed.

The particle transport component may be typically either a simple vacuum suction flow into an orifice or a vacuum suction flow into an orifice that is bounded circumferentially by a spinning vortex. The aerosol particles and dislodged target particles may be swept into the vacuum suction flow and may then be transported to a particle collecting medium associated with the particle removal system.

The particle collection component may be any of a variety of particle filters commonly utilized in connection with particle collecting techniques. Examples include, but are not limited to, a mesh filter, a woven three dimensional mesh, a filter made of commonly utilized filter materials, an absorbent surface that may be chemically coated to enhance adhesion, a vortex particle separator, an electrostatic particle collector, and an engineered material with finely etched openings to pass air but retain particles.

According to the system described herein, an apparatus for dislodging and collecting target particles from a target surface includes a reservoir of liquefied and pressurized carbon dioxide, at least one pulsed valve in communication with said reservoir, at least one expansion chamber in communication with said at least one pulsed valve for forming an aerosol mixture of frozen carbon dioxide particles and carbon dioxide gas, at least two nozzles in communication with said at least one expansion chamber for directing a spray of said aerosol mixture to substantially overlap at a single focal point downstream of said at least two nozzles, a vacuum providing a suction flow into an orifice that entrains particles from said aerosol mixture and target particles dislodged by an impact of said particles from said aerosol mixture, and a collecting medium for accumulating said particles entrained in said suction flow. The suction flow into an orifice may be surrounded circumferentially by a spinning vortex flow. The expansion chamber may include an entrance orifice that has a smaller cross section than the exit orifice. The collecting medium may include at least a filter, chemically coated adsorbing surface, metal mesh, three dimensional woven metal, metal wire, metal foil, metal and electrical insulator laminate, and/or a resistive coating on a substrate. The collecting medium may be disposed upstream of said orifice. The collecting medium may be disposed within said orifice. The reservoir may be a pressurized container of liquefied carbon dioxide gas. The pressurized liquefied carbon dioxide may form an aerosol mixture when it is converted in part to solid particles of frozen carbon dioxide and in part to carbon dioxide gas upon expansion into atmospheric pressure in the expansion chamber. The aerosol mixture may be delivered in pulses at predetermined time intervals, and said aerosol particles may be delivered in accordance with delivery of said pressurized gas. The valve may provide pulses of liquid carbon dioxide greater than 10 milliseconds and less than 1 second in duration. The vacuum may be provided by the impeller of a vortex attractor. The apparatus may also include a second supply of pressurized gas to assist the transport of said aerosol mixture. The second supply of pressurized gas may be delivered by addition into the expansion chamber or coaxially with and in the direction of the flow from the nozzle for said aerosol mixture. The second supply of pressurized gas may be air, nitrogen, argon, and/or carbon dioxide. The apparatus may also include means to assist the operator to position the apparatus at an optimal distance from the target surface. The means to position the apparatus may be ultrasonic distance measuring, at least two solid state laser pointers, and/or optical reflection sensor. The apparatus may also include means to determine if the flow of carbon dioxide liquid is sufficient for collecting target particles. The means to determine liquid flow may be temperature sensor mounted on a nozzle, optical reflection sensor viewing the reflectivity of the aerosol mixture, optical transmission sensor viewing the opacity of the aerosol mixture, and/or ultrasonic sensor to sense the density of the carbon dioxide liquid or gas.

According further to the system described herein, dislodging and collecting target particles from a target surface includes providing a frozen carbon dioxide aerosol mixture including aerosol particles dispersed in a pressurized gas, directing said aerosol mixture at said target surface including said target particles, said aerosol particles impacting said target particles causing removal of said target particles from said target surface and causing said target particles to be included in a flow of said pressurized gas with said aerosol particles, providing a suction flow into which said flow of said target particles, said aerosol particles, and said pressurized gas are directed, and collecting said particles entrained in said suction flow. Dislodging and collecting target particles from a target surface may also include delivering said pressurized gas in timed pulses and delivering said aerosol particles in accordance with said timed pulses. Dislodging and collecting target particles from a target surface may also include combining said pressurized gas with said aerosol particles to form said aerosol mixture. The suction flow may be created utilizing a vacuum suction flow into an orifice. The vacuum suction flow into an orifice may be bounded circumferentially by a spinning vortex.

BRIEF DESCRIPTION OF THE DRAWING

The system is described herein with reference to the several figures of the drawing, in which.

DETAILED DESCRIPTION

Figure 1:
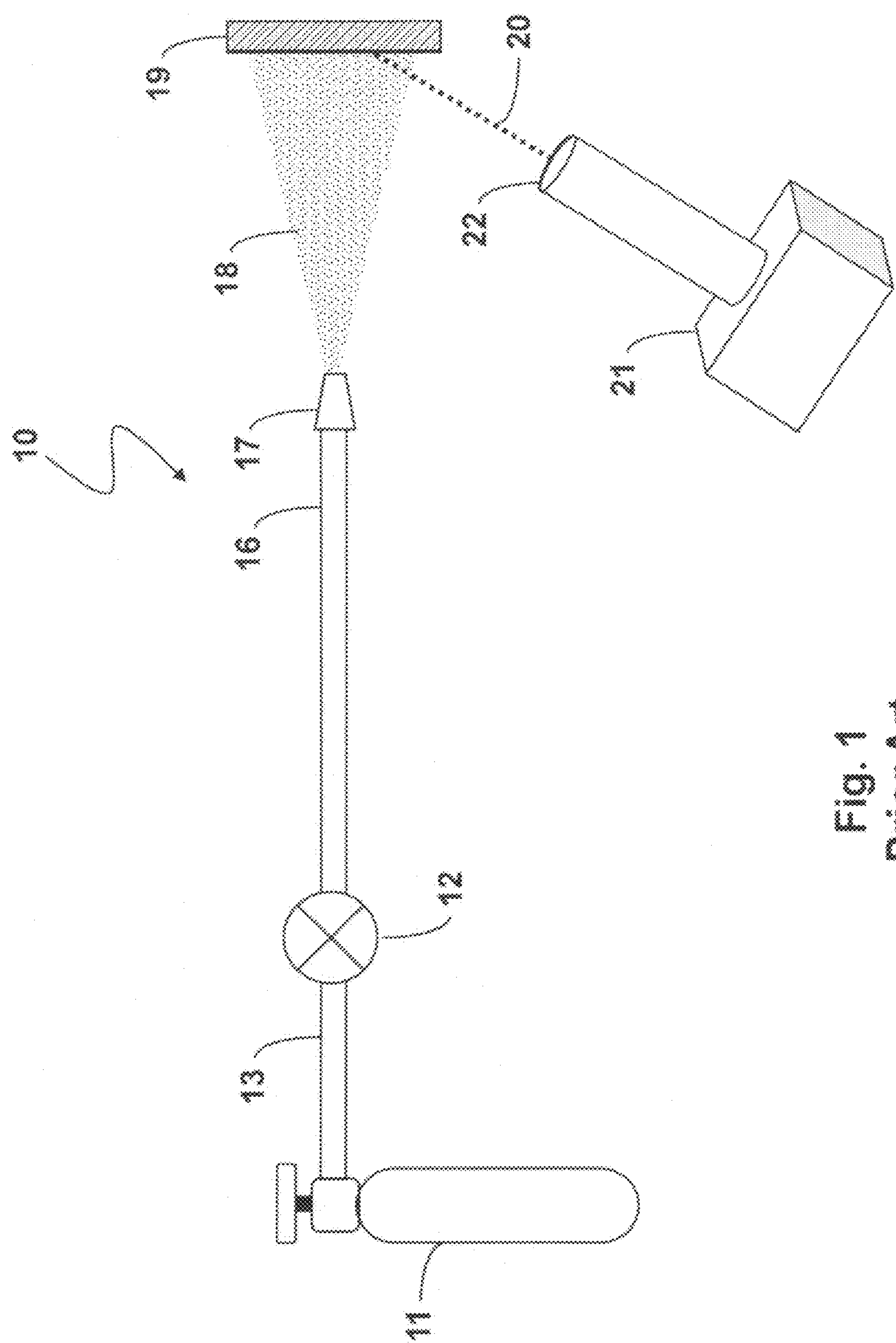
FIG. 1 is an example of an embodiment of an air jet trace particle removal system from the prior art.

Referring now to FIG. 1, shown is an example of an embodiment of an air jet trace particle removal system 10 from the prior art. The air jet system 10 includes a source of pressurized gas 11, a control valve 12, communication tubing 13, and a tube 16 in communication with an exit nozzle 17. The pressurized gas is output from nozzle 17 in an area 18. The air jet is directed by the nozzle 17 towards a target surface 19, where the air blows particles 20 off of the target surface 19, thus removing the sticky particles. Particle transport is produced by suction pump 21, whose inward flow entrains both ambient air and target particles 20. The target particles 20 are collected on a filter medium 22. When the sample has been collected, the filter medium 22 is transported to the entrance orifice of a trace chemical detector. This embodiment of the prior art is deficient in that the blowing air 18 is inefficient for removing particles from most types of target surfaces 19, and the suction pump 21 provides inefficient particle transport beyond a short distance from its entrance orifice.

Figure 2:
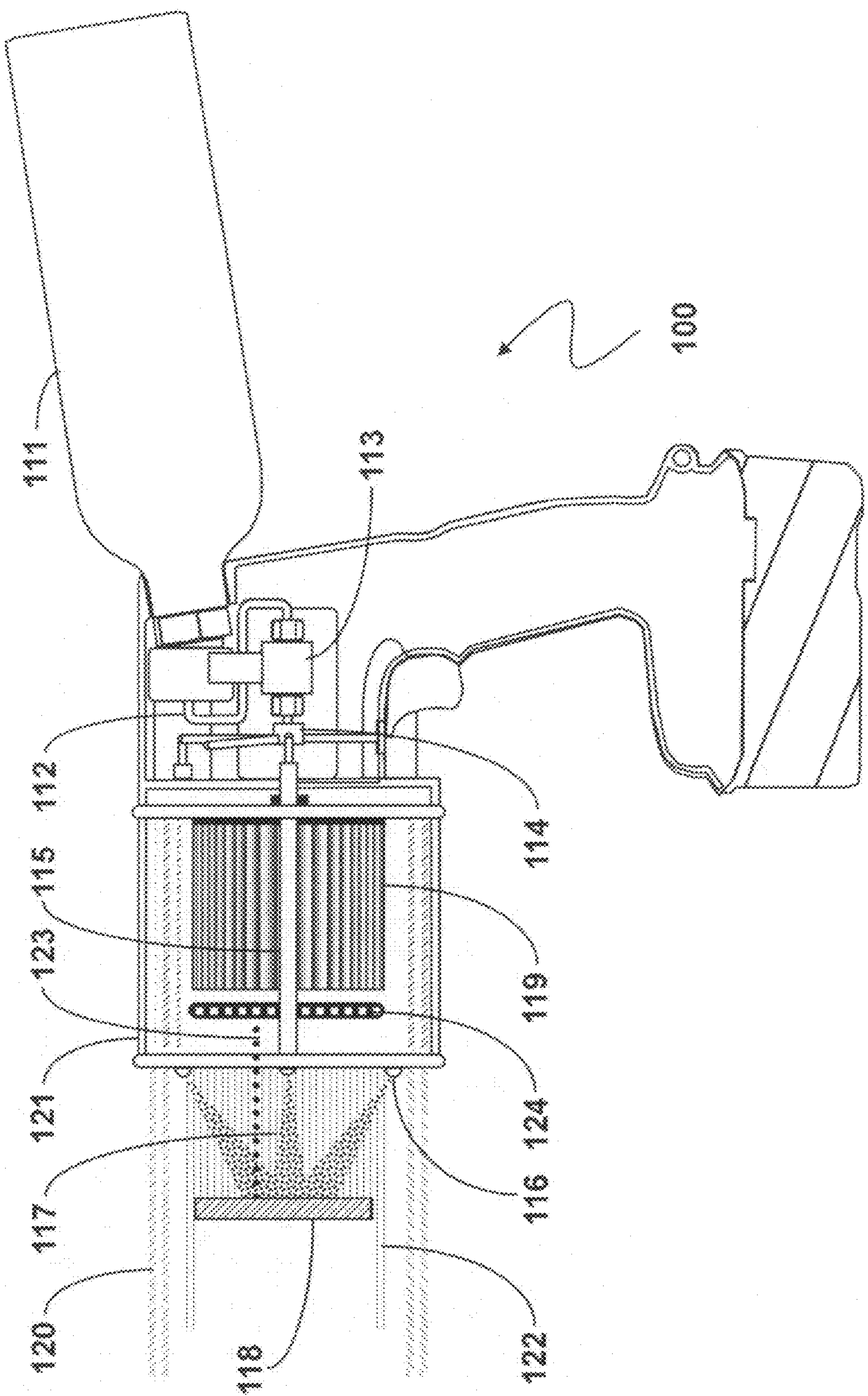
FIG. 2 is an example of an embodiment of a frozen carbon dioxide trace particle removal system that may be used in connection with the methods disclosed herein.

Referring now to FIG. 2, shown is an example of a first embodiment of a trace particle collection system that may be used in connection with the particle removal system methods described herein. While various embodiments may differ in details, FIG. 2 shows basic features of the system described herein. The particle collection system 100 illustrated in FIG. 2 is a handheld portable system, but the principles may be applied to larger, non-mobile systems. The particle removal portion of the system consists of a reservoir of liquid carbon dioxide 111, a connection tube 112, a pulsed valve 113, an expansion chamber 114, a connection tube 115 to a nozzle 116, and a spray 117 of the aerosol mixture containing frozen carbon dioxide particles and pressurized gas against the target surface 118. The particle transport portion of the system consists of an impeller fan 119 configured as a vortex attractor. The fan 119 blows an outward flowing stream of air 120 that is spinning about the axis of the impeller fan 119 and guided towards the target surface 118 by the surrounding housing 121. An inward flowing stream of air 122 entrains the trace particles 123 and transports them to the collecting substrate 124.

Although the embodiment illustrated in FIG. 2 includes three nozzles 116 and connection tubes 115 that are joined to a single expansion chamber 114, an embodiment of a particle removal component may include a varying number of these components but providing at least two nozzles for dispensing the aerosol mixture. The at least two nozzles 116 may be aimed to focus their aerosol mixture sprays 117 at a common point, as shown in FIG. 2. This focal point may be located a short distance beyond the target surface 118. When configured in this manner, the aerosol mixture sprays 117 interact with one another and the target surface 118 and reflect a substantial portion of the aerosol mixture spray 117 back towards the collection substrate 124. If only one nozzle 116 were employed, the interaction of the aerosol mixture spray 117 and the target surface 118 could cause the spray 117 to spread radially outward parallel to the target surface 118, rather than towards the collection substrate 124.

The aerosol particles may be frozen carbon dioxide. The frozen carbon dioxide aerosol particles may sublime at ambient temperature. The release of liquid carbon dioxide from the pulsed valve 113 into the expansion chamber 114 allows a first portion of the liquid to absorb energy and become gaseous carbon dioxide and a second portion of the liquid to release energy and freeze into small particles of frozen carbon dioxide, thus forming the aerosol mixture spray 117.

The frozen carbon dioxide aerosol mixture 117 may be selected to provide no significant damage to the target surface. For example, a semiconductor wafer with a circuit device pattern can generally be sprayed without damage to the circuit. The carbon dioxide aerosol mixture 117 is an oxide and has no flashpoint, which may be noted as an important characteristic when working with finely divided materials. The carbon dioxide aerosol mixture spray 117 contains carbon dioxide gas, which displaces oxygen and does not support flames. The carbon dioxide aerosol mixture 117 may be non-toxic and harmless to humans and animals, as long as not directed into the eyes. The frozen carbon dioxide aerosol mixture 117 may be pulsed to avoid excessive emissions into a confined space, since the carbon dioxide gas residue may displace the oxygen in air.

The embodiments of the aerosol generator illustrated in connection with FIGS. 2 through 4 include a source of pressurized gas to blow the aerosol particle spray towards a target surface that may be contaminated with traces of target chemicals, such as narcotics or explosives. The source of pressurized gas may be operated continuously or may be pulsed. A typical pulse may be between 0.01 seconds and 1 second so that gas and aerosol particles are delivered in accordance with the pulse timing.

Besides the carbon dioxide gas provided by the expansion chamber 114, optionally an additional source of pressurized gas may be combined to act as an accelerant, to isolate the frozen carbon dioxide particles from the ambient warm air and thus sublime at a slower rate, or to enable the aerosol mixture spray to propagate to a greater distance from the nozzle. The optional additional source of pressurized gas may be combined with the carbon dioxide aerosol mixture in the expansion chamber 114, or it may be provided coaxially surrounding and directed substantially parallel with and in the direction of the flow from the nozzle 116 orifice. The pressure of the optional pressurized gas may be less than 120 pounds per square inch, a value easily obtained with small compressors. Significantly higher or lower pressures may also be utilized in accordance with the availability, cost, and safety restrictions for the pressurized gas. For example, a high pressure tank of gas may not be acceptable in a public area due to the risk of explosion caused by mishandling. An embodiment may use any one of a variety of different gases including, for example, air, nitrogen, argon, and carbon dioxide. An embodiment may also utilize one or more of the foregoing in a combination alone, or with one or more other gases.

Figure 3:
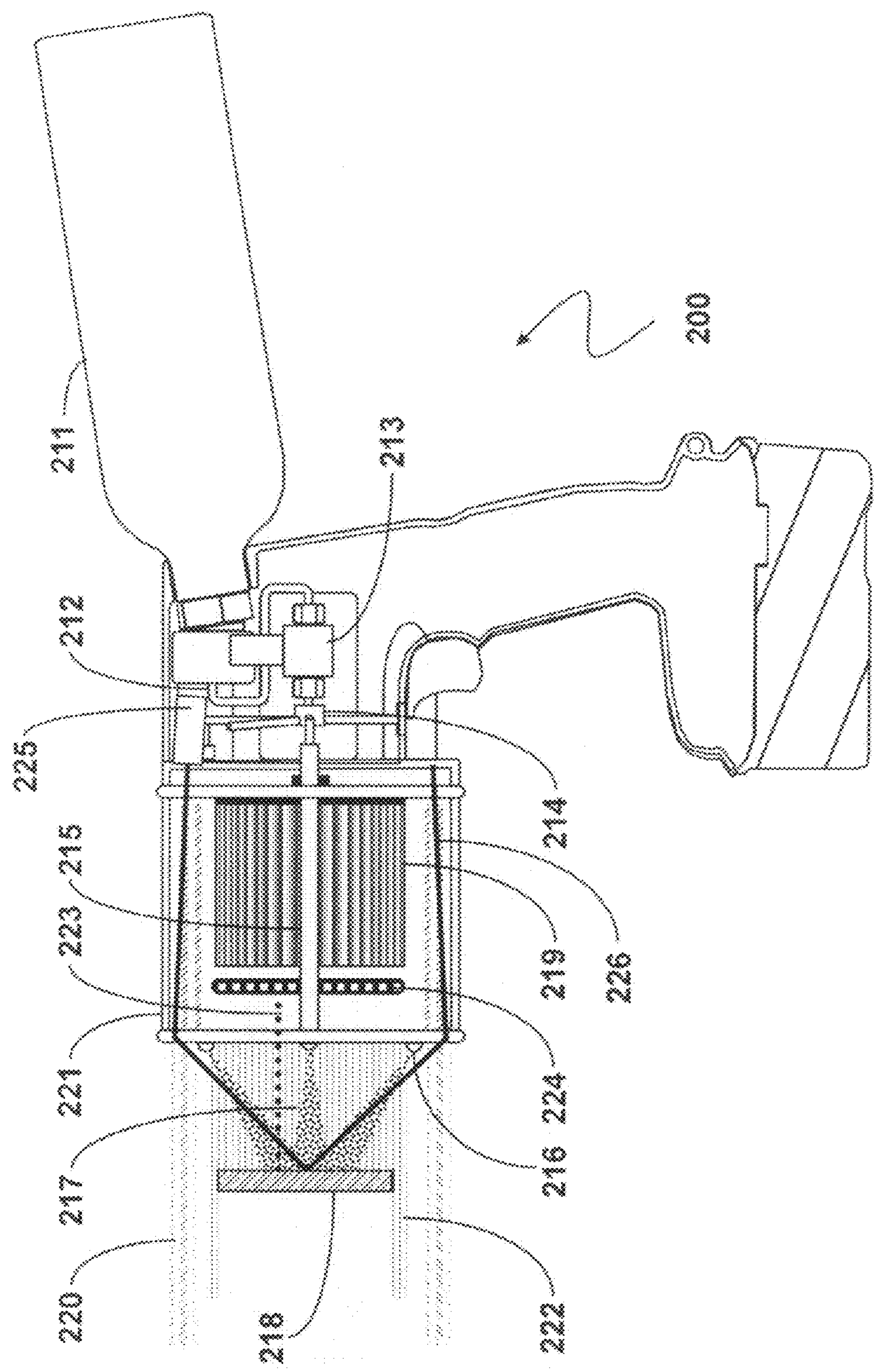
FIG. 3 is an example of a second embodiment of a frozen carbon dioxide trace particle removal system that may be used in connection with the system described herein.
Figure 4:
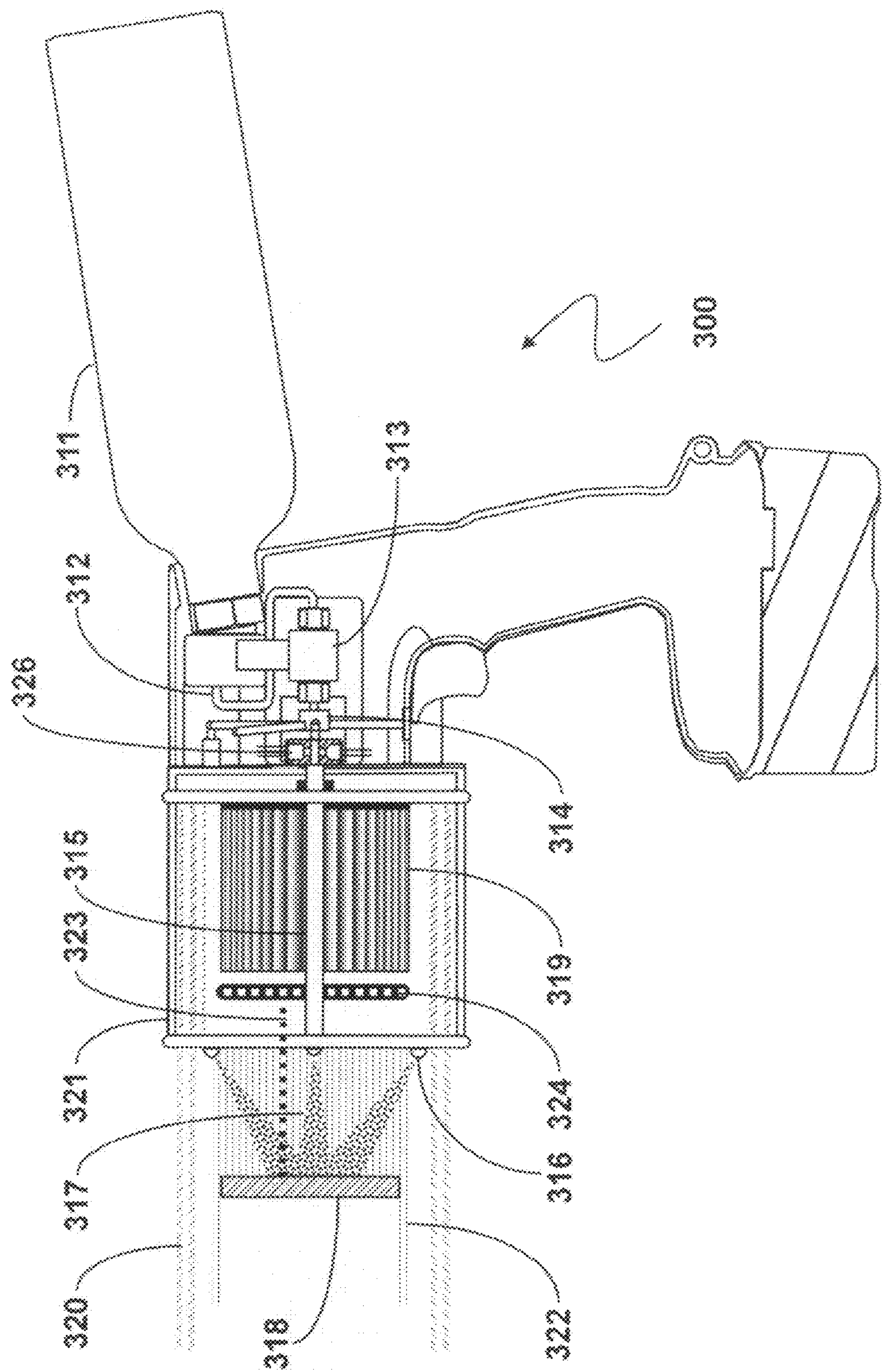
FIG. 4 is an example of a third embodiment of a frozen carbon dioxide trace particle removal system that may be used in connection with the system described herein.

The nozzles 116, 216, and 316 of FIGS. 2 through 4 provide for guiding the mixture of aerosol particles and blowing gas towards a point on a target surface such that this point is the object of the particle transport component of the particle removal system, described in more detail in following paragraphs.

The frozen carbon dioxide aerosol particles may impact the target particles on a target surface and provide sufficient momentum transfer to dislodge the target particles from the target surface and become entrained in the accompanying puff of carbon dioxide gas transporting the aerosol particles. The dislodged target particles and aerosol particles may then be collected by the particle transport component. The frozen carbon dioxide aerosol mixture may release target particles by at least one of: physical impact between the aerosol particle and the target particle, sudden sublimation producing a local pulse of gas when the aerosol particle contacts a surface at room temperature, the pulse of pressurized gas accompanying the aerosol mixture, and cooling the target particle such that its adhesion properties are changed.

The collecting substrate 124 may be any one of a variety of different materials and may vary in accordance with whether an embodiment electrically charges the collecting medium 124. The collecting medium may be a filter. The collecting medium may include one or more of the following: a chemically coated adsorbing surface, a metal mesh, a three dimensional woven metal, a metal wire, a metal foil, a metal and electrical insulator laminate, and/or or a resistive coating on a substrate. Examples of non-electrically conducting collecting media include materials fabricated from cotton, paper, aramids, polyimides, fluorocarbons, and silica. Examples of metals and metal coatings include stainless steel, aluminum, titanium, nickel, chromium, silver, carbon, platinum, and gold.

The particle collection component may be any of a variety utilized in connection with particle collecting techniques. Examples include, but are not limited to, a mesh filter, a woven three dimensional mesh, a filter made of commonly utilized filter materials, an absorbent surface that may be chemically coated to enhance adhesion, a vortex particle separator, an electrostatic particle collector, and an engineered material with finely etched openings to pass air or another gas, but which also is capable or retaining particles.

In an embodiment, the particle transport component may be, for example, a simple vacuum suction flow into a nozzle or a vacuum suction flow into a nozzle that is bounded circumferentially by a spinning vortex. The aerosol particles and dislodged target particles may be swept into the vacuum suction flow and may then be transported to a particle collecting medium associated with the particle removal system.

Referring now to FIG. 3, shown is an example of a second embodiment of a trace particle collection system that may be used in connection with the particle removal system methods described herein. While various embodiments may differ in details, FIG. 3 shows basic features of the system described herein. The particle collection system 200 illustrated in FIG. 3 is a handheld portable system, but the principles may be applied to larger, non-mobile systems. The particle removal portion of the system consists of a reservoir of liquid carbon dioxide 211, a connection tube 212, a pulsed valve 213, an expansion chamber 214, a connection tube 215 to a nozzle 216, and a spray 217 of the aerosol mixture containing frozen carbon dioxide particles and pressurized carbon dioxide gas against the target surface 218. The particle transport portion of the system consists of an impeller fan 219 configured as a vortex attractor. The fan 219 blows an outward flowing stream of air 220 that is spinning about the axis of the impeller fan 219 and guided towards the target surface 218 by the surrounding housing 221. An inward flowing stream of air 222 entrains the trace particles 223 and transports them to the collecting substrate 224.

FIG. 3 further illustrates the use of an aid provided to the operator for determining the optimal distance of the trace particle collection system from the target surface 218. In this embodiment, two solid state lasers 225 have their beams 226 oriented to converge to a common focal point when the target surface 218 is at the correct distance. Other possible embodiments may utilize an ultrasonic distance detector or an optical reflection sensor. These other possible embodiments require a means to inform the operator when the optimal distance has been achieved. The means may be in visual form, such as an illuminated indicator, audible form, such as a distinctive sound, or in tactile form, such as a vibrator.

It should be noted that the optimal distance indicator may be any one of a variety of different types of sensors in accordance with the particular application using the techniques described herein and/or described in patents and/or pending patent applications that are incorporated by reference herein.

Referring now to FIG. 4, shown is an example of a third embodiment of a trace particle collection system that may be used in connection with the particle removal system methods described herein. While various embodiments may differ in details, FIG. 4 shows basic features of the system described herein. The particle collection system 300 illustrated in FIG. 4 is a handheld portable system, but the principles may be applied to larger, non-mobile systems. The particle removal portion of the system consists of a reservoir of liquid carbon dioxide 311, a connection tube 312, a pulsed valve 313, an expansion chamber 314, a connection tube 315 to a nozzle 316, and a spray 317 of the aerosol mixture containing frozen carbon dioxide particles and pressurized carbon dioxide gas against the target surface 318. The particle transport portion of the system consists of an impeller fan 319 configured as a vortex attractor. The fan 319 blows an outward flowing stream of air 320 that is spinning about the axis of the impeller fan 319 and guided towards the target surface 318 by the surrounding housing 321. An inward flowing stream of air 322 entrains the trace particles 323 and transports them to the collecting substrate 324.

FIG. 4 further illustrates the use of a liquid carbon dioxide sensor to provide information to the operator when the liquid carbon dioxide has expired and the carbon dioxide aerosol mixture is no longer being produced. In this embodiment, an optical transmission sensor 326 is employed on a connection tube 315. The optical transmission sensor 326 views the contents of the connection tube 315 through a transparent section of the connection tube 315. If only carbon dioxide gas is entering the connection tube 315, the contents will be optically transparent and provide a first signal level. If the tube contains a carbon dioxide aerosol mixture, the contents will be optically reflective and provide a second signal level.

Other possible embodiments for providing a liquid carbon dioxide sensor may be provided. For example, a temperature sensor may be mounted on a nozzle to sense the cold temperature resulting from the frozen carbon dioxide, an optical reflection sensor may view the difference in reflectivity of carbon dioxide gas versus the carbon dioxide aerosol mixture, and an ultrasonic sensor may be used to sense the presence of higher density of the carbon dioxide liquid compared to carbon dioxide gas.

All of the possible embodiments for providing a liquid carbon dioxide sensor require a means to inform the operator when the liquid carbon dioxide has expired. The means may be in visual form, such as an illuminated indicator, audible form, such as a distinctive sound, or in tactile form, such as a vibrator.

The system described herein may incorporate other features, such as features described in commonly assigned copending and/or issued U.S. patents and/or patent applications incorporated by reference herein, including without limitation features described in commonly-assigned U.S. Pat. No. 7,098,672 to Belyakov, et al., entitled "Flash vapor sampling for a trace chemical detector", U.S. Pat. No. 7,244,288 to Belyakov, et al., entitled "Pulsed vapor desorber", U.S. Pat. No. 6,888,128 to Krasnobaev, et al., entitled "Virtual wall gas sampling for an ion mobility spectrometer", U.S. Pat. No. 6,870,155 to Krasnovaev, et al., entitled "Modified vortex for an ion mobility spectrometer", U.S. Pat. No. 6,861,646 to Motchkine, et al., entitled "Cyclone sampling nozzle for an ion mobility spectrometer", and U.S. Pat. No. 6,828,795 to Krasnobaev, et al., entitled "Explosive detection system", U.S. Published Patent App. No. 2006-0214580 A1 to Bunker, et al., entitled "Photoelectric ion source photocathode regeneration system", and U.S. Published Patent App. No. 2003-0155504 A1 to Motchkine, et al., entitled "Radiative sample warming for an ion mobility spectrometer", all of which are incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A handheld portable apparatus for dislodging and collecting target particles from a target surface, the apparatus comprising:

a reservoir of liquefied and pressurized carbon dioxide;

at least one pulsed valve in communication with said reservoir;

at least one expansion chamber in communication with said at least one pulsed valve for forming an aerosol mixture of frozen carbon dioxide particles and carbon dioxide gas;

at least two nozzles in communication with said at least one expansion chamber for directing a spray of said aerosol mixture to substantially overlap at a single focal point downstream of said at least two nozzles;

a particle transport component providing a suction flow into an orifice that entrains particles from said aerosol mixture and target particles dislodged by an impact of said particles from said aerosol mixture;

a collecting medium for accumulating said particles entrained in said suction flow; and a position-assisting device that assists the operator to position the handheld portable apparatus at an optimal distance from the target surface, wherein the optimal distance is based on the single focal point of the aerosol mixture sprays from the at least two nozzles being located beyond the target surface.

2. The apparatus of claim 1, wherein said suction flow into an orifice is surrounded circumferentially by a spinning vortex flow.

3. The apparatus of claim 1, wherein said expansion chamber includes an entrance orifice that has a smaller cross section than the exit orifice.

4. The apparatus of claim 1, wherein the collecting medium includes at least one of a filter, chemically coated adsorbing surface, metal mesh, three dimensional woven metal, metal wire, metal foil, metal and electrical insulator laminate, or a resistive coating on a substrate.

5. The apparatus of claim 1, wherein the collecting medium is disposed upstream of said orifice.

6. The apparatus of claim 1, wherein the collecting medium is disposed within said orifice.

7. The apparatus of claim 1, wherein said reservoir is a pressurized container of liquefied carbon dioxide gas.

8. The reservoir of claim 1, wherein said pressurized liquefied carbon dioxide forms an aerosol mixture when it is converted in part to solid particles of frozen carbon dioxide and in part to carbon dioxide gas upon expansion into atmospheric pressure in the expansion chamber.

9. The apparatus of claim 8, wherein said aerosol mixture is delivered in pulses at predetermined time intervals, and said aerosol particles are delivered in accordance with delivery of said pressurized gas.

10. The apparatus of claim 9, wherein said valve provides pulses of liquid carbon dioxide greater than 10 milliseconds and less than 1 second in duration.

11. The apparatus of claim 1, wherein said article transport component includes an impeller of a vortex attractor.

12. The apparatus of claim 1, further including a second supply of pressurized gas to assist the transport of said aerosol mixture.

13. The apparatus of claim 12, wherein said second supply of pressurized gas is delivered by at least one of: addition into said expansion chamber, or addition coaxial with and in the direction of the flow from at least one of said at least two nozzles for said aerosol mixture.

14. The apparatus of claim 12, wherein said second supply of pressurized gas is at least one of: air, nitrogen, argon, carbon dioxide.

15. The apparatus of claim 1, wherein said position-assisting device is at least one of: an ultrasonic distance measuring device, at least two solid state laser pointers, or an optical reflection sensor.

16. The apparatus of claim 1, further including a flow-determining device that determines if the flow of carbon dioxide liquid is sufficient for collecting target particles.

17. The apparatus of claim 16, wherein said flow-determining device is at least one of: temperature sensor mounted on a nozzle, optical reflection sensor viewing the reflectivity of the aerosol mixture, optical transmission sensor viewing the opacity of the aerosol mixture, ultrasonic sensor to sense the density of the carbon dioxide liquid or gas.

18. A method for dislodging and collecting target particles from a target surface, the method comprising:

providing a frozen carbon dioxide aerosol mixture including aerosol particles dispersed in a pressurized gas;

directing said aerosol mixture at said target surface including said target particles, said aerosol particles impacting said target particles causing removal of said target particles from said target surface and causing said target particles to be included in a flow of said pressurized gas with said aerosol particles;

providing a suction flow into which said flow of said target particles, said aerosol particles, and said pressurized gas are directed; and collecting said particles entrained in said suction flow on a substrate.

19. The method of claim 18, the method further comprising:

delivering said pressurized gas in timed pulses; and delivering said aerosol particles in accordance with said timed pulses.

20. The method of claim 18, further comprising:

combining said pressurized gas with said aerosol particles to form said aerosol mixture.

21. The method of claim 18, wherein said suction flow is created utilizing a vacuum suction flow into an orifice.

22. The method of claim 21, wherein said vacuum suction flow into an orifice is bounded circumferentially by a spinning vortex.

* * * * *